(12) United States Patent
Tripathi et al.

(10) Patent No.: US 11,345,664 B2
(45) Date of Patent: May 31, 2022

(54) PROCESS FOR THE PREPARATION OF (S)-NETARSUDIL, ITS SALTS AND POLYMORPHS

(71) Applicant: Micro Labs Ltd., Karnataka (IN)

(72) Inventors: Punit Tripathi, Karnataka (IN); Golla Maghava, Karnataka (IN); Brijesh Kumar, Karnataka (IN); Peyalla Divya, Karnataka (IN); Lalit Kumar, Karnataka (IN); Thaslim Basha, Karnataka (IN); Arun Kumar Awasthi, Karnataka (IN); Pramod Kumar, Karnataka (IN)

(73) Assignee: Micro Labs Ltd., Bangalore (IN)

( * ) Notice: Subject to any disclaimer, the term of this patent is extended or adjusted under 35 U.S.C. 154(b) by 140 days.

(21) Appl. No.: 16/913,452

(22) Filed: Jun. 26, 2020

(65) Prior Publication Data
US 2021/0094918 A1  Apr. 1, 2021

(51) Int. Cl.
*C07D 217/22* (2006.01)
*C07D 209/48* (2006.01)

(52) U.S. Cl.
CPC ......... *C07D 217/22* (2013.01); *C07D 209/48* (2013.01); *C07B 2200/13* (2013.01)

(58) Field of Classification Search
CPC ............................ C07D 217/22; C07D 209/48
See application file for complete search history.

(56) References Cited

U.S. PATENT DOCUMENTS

| 8,394,826 B2 * | 3/2013 | deLong .................... A61P 9/00 514/307 |
| 9,643,927 B1 | 5/2017 | Sturdivant et al. |
| 9,963,432 B2 * | 5/2018 | Sturdivant ........... C07D 217/24 |
| 2018/0215715 A1 | 8/2018 | Mainfeld et al. |
| 2019/0322625 A1 | 10/2019 | deLong et al. |

FOREIGN PATENT DOCUMENTS

CN  107434780 A  12/2017

OTHER PUBLICATIONS

Dai, Org Chem Front, 2017, vol. 4, 297-302. (Year: 2017).*
Sturdivant, Bioorg & MEd Chem Lett, vol. 26, 2016, 2475-2480. (Year: 2016).*

* cited by examiner

*Primary Examiner* — D Margaret M Seaman
(74) *Attorney, Agent, or Firm* — Katten Muchin Rosenman LLP (57) ABSTRACT

The present invention relates to a process for the preparation of (S)-Netarsudil or its pharmaceutically acceptable salts using novel intermediates. The present invention further provides novel salts, novel intermediates and novel polymorphic forms of the (S)-Netarsudil salts and process for the preparation of the same.

20 Claims, 5 Drawing Sheets

PROCESS FOR THE PREPARATION OF (S)-NETARSUDIL, ITS SALTS AND POLYMORPHS

CROSS-REFERENCE TO RELATED APPLICATIONS

This application claims benefit of Indian application 201941026065, filed Jun. 29, 2019, which is herein incorporated by reference in its entirety for all purposes.

FIELD OF THE INVENTION

The present invention relates to a process for the preparation of (S)-Netarsudil or its pharmaceutically acceptable salts using novel intermediates. The present invention further provides novel salts, novel intermediates and novel polymorphic forms of the (S)-Netarsudil salts and process for the preparation of the same.

BACKGROUND OF THE INVENTION

Netarsudil dimesylate is chemically known as (S)-4-(3-amino-1-(isoquinolin-6-yl-amino)-1-oxopropan-2-yl)benzyl-2,4-dimethylbenzoate dimesylate and is represented by following Formula I, Formula I Approved form of Netarsudil dimesylate has one chiral centre wherein the (S)-enantiomer is the desired form, hereinafter referred as (S)-Netarsudil.

(S)-Netarsudil dimesylate is a Rho kinase inhibitor and is indicated for the reduction of elevated intraocular pressure in patients with open-angle glaucoma or ocular hypertension.

U.S. Pat. No. 8,394,826B2 provides a process for the preparation of Netarsudil as its dihydrochloride salt. The said process involves preparation of racemic Boc-protected Netarsudil and then separating the R and S enantiomers by supercritical fluid chromatography (Chiralpak AS-H column, eluent: 18.8% MeOH, 0.2% dimethylethylamine, 80% $CO_2$). The (S)-enantiomer of Boc-protected Netarsudil thus obtained was deprotected with HCl/dioxane in dichloromethane to obtain Netarsudil dihydrochloride having an enantiomeric excess of greater than 98%. Use of supercritical fluid chromatography makes this process difficult for bulk manufacturing and affects the overall yield as well, thus making it uneconomical.

Apart from the above, U.S. Pat. No. 9,643,927B2 and Chinese Patent Publication No. 107434780 provide a process for the preparation of Netarsudil as its dimesylate salt. The process described therein, involves the use of chiral auxiliary reagents such as oxazolidinone derivatives to obtain the desired chirality at intermediate stage which on further conversion gave the (S)-enantiomer of Netarsudil.

US Publication No. 2018/0215715A1 provides polymorphic forms N1, N2, N3, N4, N5, N6, and N7 of Netarsudil dimesylate and process for their preparation. The process reported in this publication involves a lengthy processing time.

US Publication No. 2019/0322625A1 provides process for the preparation of certain mono-(acid) salts of (S)-Netarsudil and racemic Netarsudil.

The prior reported processes for the preparation of (S)-Netarsudil have one or more disadvantages such as lengthy reaction time, use of silica column chromatography for isolation and purification of intermediate(s), large number of synthetic steps, and low overall yield which makes these processes nonviable and uneconomical for bulk manufacturing.

The present invention proposes a novel process for the preparation of highly pure (S)-Netarsudil or its pharmaceutically acceptable salts wherein the said process is cost effective, industrially viable, and provides high yield. Further present invention proposes a novel salts, novel intermediates and novel polymorphic forms of the (S)-Netarsudil salts and process for the preparation of the same.

OBJECTIVES OF THE INVENTION

The main objective of the present invention is to provide a process for the preparation of (S)-Netarsudil or its pharmaceutically acceptable salts using novel intermediates.

Another objective of the present invention is to provide novel intermediates for the synthesis of (S)-Netarsudil and process for their preparation.

Another objective of the present invention is to provide novel salts of (S)-Netarsudil, their polymorphs and process for preparation thereof.

Another objective of the present invention is to provide a highly stable form of (S)-Netarsudil dimesylate.

SUMMARY OF THE INVENTION

An aspect of the present invention relates to a process for the preparation of (S)-Netarsudil of Formula 1 or pharmaceutically acceptable salts thereof, Formula 1 comprising conversion of compound of Formula 2 or a salt thereof to (S)-Netarsudil or its pharmaceutically acceptable salts,

Formula 2 wherein $R^1$ is selected from the group consisting of hydrogen, halogen, 2,4-dimethyl benzoyloxy, and hydroxyl; $R^2$ is selected from the group consisting of hydroxyl, $C_1$-$C_5$ alkoxy, halogen, chiral auxiliary group and isoquinolin-6-yl-amino.

Another aspect of the present invention relates to novel intermediates of Formula 2 or salts thereof that are useful for the preparation of (S)-Netarsudil or its pharmaceutically acceptable salts.

Further aspect of the present invention relates to a process for the preparation of compound of Formula 2 or salts thereof, comprising reacting a compound of Formula 3 with a compound of Formula 4, Formula 3

Formula 4 wherein $R^1$ is selected from the group consisting of hydrogen, halogen, 2,4-dimethyl benzoyloxy and hydroxyl; X is halogen; and a chiral auxiliary group is a non-racemic functional group that imparts a diastereoselective reaction at a prochiral centre of a molecule.

A further aspect of the present invention provides monomesylate and (−)-O,O′-di-p-toluoyl-L-tartrate salt of (S)-Netarsudil and process for their preparation.

Another aspect of the present invention provides a highly stable form of (S)-Netarsudil dimesylate and process for its preparation.

DETAILED DESCRIPTION OF THE INVENTION

Before the present invention is described, it is to be understood that unless defined otherwise, all technical and scientific terms used herein have the same meaning as commonly understood by one of ordinary skill in the art to which this invention belongs. Further, it is to be understood that the present invention is not limited to the methodologies and materials similar or equivalent to those described herein. The preferred methods and materials are described and these may vary within the specification as indicated. Unless stated to the contrary, any use of the words such as "including", "comprising", "having" and the like, means "including without limitation" and shall not be construed to limit any general statement that it follows to the specific or similar items or matters immediately following it. Embodiments of the invention are not mutually exclusive but may be implemented in various combinations. The described embodiments of the invention and the disclosed examples are given for the purpose of illustration rather than limitation of the invention as set forth in the appended claims. Further the disclosed embodiments are merely exemplary methods of the invention, which may be embodied in various forms.

The term "about", as used herein, refers to any value which lies within the range defined by a number up to ±10% of the value.

The term "chiral auxiliary group" as used herein, refers to a non-racemic functional group that imparts a distereoselective reaction at a prochiral centre of a molecule. The chiral auxiliary group can be heterocyclic chiral amine not limiting to (R)-(−)-4-phenyl-2-oxazolidinone; (S)-(+)-4-phenyl-2-oxazolidinone, (R)-(−)-4-benzyl-2-oxazolidinone, (S)-(+)-4-benzyl-2-oxazolidinone, (S)-(+)-4-methyl-2-oxazolidinone, (R)-(+)-4-methyl-2-oxazolidinone, (R)-(+)-4-isopropyl-2-oxazolidinone, (S)-(+)-4-isopropyl-2-oxazolidinone, (2R)-2-(4-methylphenyl)pyrrolidine, (2 S)-2-(4-methylphenyl)pyrrolidine, (R)-(−)-2-methylpyrrolidine, (S)-(+)-2-methylpyrrolidine, (S)-(−)-N-benzylpyrrolidine-2-methanol, (R)-(+)-N-benzylpyrrolidine-2-methanol; or aromatic chiral amine not limiting to (S)-(−)-1-(1-naphthyl) ethylamine, (R)-(+)-1-(1-naphthyl)ethylamine, (S)-(−)-α-methylbenzylamine, (R)-(+)-α-methylbenzylamine; or cyclic chiral amine not limiting to (R)-(−)-1-cyclohexyl ethyl amine, (S)-(+)-1-cyclohexyl ethyl amine, (1R,2R)-1-amino-2-benzloxycyclopentane, acyclic chiral amine not limiting to (R)-2-aminopentane, (R)-(−)-2-aminobutane.

The term "halogenating agent", as used herein, is selected from but not limited to N-bromosuccinimide (NBS), N-chlorosuccinimide (NCS), N-iodosuccinimide (NIS), 1,3-dibromo-5,5-dimethylhydantoin (DBDMH).

The term "coupling agent" as used herein, is selected from but not limited, to 2,2,2-trichloro-1,1-dimethylethylchloroformate, 1-ethyl-3-(3-dimethylaminopropyl) carbodiimide (EDC), N,N'-dicyclohexylcarbodiimide (DCC), N,N'-diisopropylcarbodiimide (DIC), 1,1'-carbonyldiimidazole (CDI), 1-propanephosphonic anhydride (T3P), hydroxybenzotriazole (HOBt), 1-[Bis(dimethylamino)methylene]-1H-1,2,3-triazolo[4,5-b]pyridinium-3-oxide hexafluorophosphate

(HATU), 3-[bis(dimethylamino)methyliumyl]-3H-benzotriazol-1-oxide hexafluorophosphate (HBTU).

The term "base" as used herein includes organic or inorganic bases. Inorganic bases include hydroxides, carbonates and bicarbonates of alkali & alkaline earth metals such as sodium hydroxide, lithium hydroxide, potassium hydroxide, sodium carbonate, potassium carbonate, cesium carbonate, sodium bicarbonate, potassium bicarbonate, calcium bicarbonate or the like; alkali metal hydrides such as sodium hydride, potassium hydride, lithium hydride or the like; ammonia, ammonium hydroxide, ammonium carbonate, ammonium bicarbonate or mixture thereof. Organic bases include triethyl amine, pyridine, collidine, 4-dimethylaminopyridine, lithium bis(trimethylsilyl)amide, n-butyl lithium or a mixture thereof.

The term "solvent", as used herein, refers to any solvent or solvent mixtures, including, for example water, aromatic hydrocarbons, aliphatic hydrocarbons, alcohols, esters, halogenated hydrocarbons, ketones, ethers, polar aprotic solvents, or mixtures thereof. Examples of aromatic hydrocarbons include but are not limited to benzene, toluene and xylene. Examples of aliphatic hydrocarbons include but are not limited to hexane, and heptane. Examples of alcohols include but are not limited to methanol, ethanol, isopropanol, and butanol. Examples of esters include but are not limited to ethyl acetate, n-propyl acetate, isopropyl acetate, and n-butyl acetate. Examples of halogenated hydrocarbons include but are not limited to dichloromethane, chloroform, carbon tetrachloride, and 1,2-dichloroethane. Examples of ketones include but are not limited to acetone and methyl ethyl ketone. Examples of ethers include but are not limited to diethyl ether, dioxane, and tetrahydrofuran. Examples of polar aprotic solvents include but are not limited to N,N-dimethylformamide, N,N-dimethylacetamide, dimethyl sulphoxide, acetonitrile, and N-methylpyrrolidone.

An aspect of the present invention provides a process for the preparation of (S)-Netarsudil of Formula 1 or pharmaceutically acceptable salts thereof, Formula 1 comprising conversion of compound of Formula 2 or a salt thereof to (S)-Netarsudil or its pharmaceutically acceptable salts, Formula 2 wherein $R^1$ is selected from the group consisting of hydrogen, halogen, 2,4-dimethyl benzoyloxy, and hydroxyl; $R^2$ is selected from the group consisting of hydroxyl, $C_1$-$C_5$ alkoxy, halogen, a chiral auxiliary group and isoquinolin-6-yl-amino.

Process for conversion of compound of Formula 2 to (S)-Netarsudil or pharmaceutically acceptable salts thereof comprises obtaining a compound of formula 2 wherein $R^1$ is 2,4-dimethyl benzoyloxy and $R^2$ is isoquinolin-6-yl amino followed by deprotection.

In an embodiment, compound of Formula 2 wherein $R^1$ is hydrogen is converted to $R^1$ as 2,4-dimethyl benzoyloxy through halogenation followed by esterification with 2,4-dimethyl benzoic acid.

In another embodiment, a compound of Formula 2 wherein $R^1$ is halogen or hydroxyl is converted to $R^1$ as 2,4-dimethyl benzoyloxy through esterification with 2,4-dimethyl benzoic acid.

The halogenation of compound 2 is carried out with a halogenating agent selected from the list described above, preferably 1,3-dibromo-5,5-dimethylhydantoin in a solvent preferably halogenated hydrocarbon solvent, at a temperature from about 20° C. to reflux temperature.

The said halogenation is done optionally in the presence of radical initiator selected from the group comprising of inorganic peroxide such as ammonium persulfate, organic peroxide such as benzoyl peroxide or azo compounds such as azobisisobutyronitrile or a combination thereof.

In an embodiment, wherein the esterification is preferably performed in the presence of a base in a solvent at a temperature from about 20° C. to reflux temperature. The base is selected from group as defined above, preferably alkali and alkaline earth metal hydroxide, carbonate or bicarbonate.

In another embodiment, compound of Formula 2 having $R^2$ as chiral auxiliary is converted to $R^2$ as isoquinolin-6-yl amino through hydrolysis followed by condensation with 6-aminoisoquinoline.

The hydrolysis of compound of Formula 2 (having $R^1$ as defined above and $R^2$ as chiral auxiliary group) involves treating the compound of Formula 2 with alkali metal hydroperoxide prepared in situ by reacting alkali metal hydroxide with hydrogen peroxide or methods known in the literature. Preferably the alkali metal hydroperoxide is lithium hydroperoxide which is effective to remove the chiral auxiliary group selectively.

The condensation of compound of Formula 2 (having $R^1$ as defined above and $R^2$ as hydroxyl) with 6-aminoisoquinoline involves treating the compound of Formula 2 with 6-aminoisoquinoline in the presence of coupling agent as defined above earlier, preferably trichlorodimethyl ethylchloroformate and a base as defined above earlier, preferably collidine in a suitable solvent at a temperature from about −20° C. to reflux temperature.

In another embodiment, deprotection of compound of Formula 2 having $R^1$ as 2,4-dimethyl benzoyloxy and $R^2$ as isoquinolin-6-yl amino to obtain (S)-Netarsudil involves treating the said compound of Formula 2 with a deprotecting agent known in the literature preferably but not limited to hydrazine hydrate in a suitable solvent at a temperature from about −20° C. to reflux temperature for a time period sufficient to complete the reaction.

After the completion of reaction, (S)-Netarsudil can be isolated by the common isolation techniques such as cooling, extraction, washing, crystallization, precipitation, filtration, filtration under vacuum, decantation and centrifugation, or combinations thereof.

(S)-Netarsudil of Formula 1 can be further converted to its pharmaceutically acceptable salts by treating with suitable acid selected from methane sulfonic acid, (R) or (S)-camphor sulfonic acid, (R) or (S)-(−)-O,O'-di-p-toluoyl-L-tartaric acid in a solvent at a temperature from 5° C. to reflux temperature to obtain the corresponding salt.

In an embodiment of this aspect, the preferable salt of (S)-Netarsudil is (S)-Netarsudil hemi(−)-O,O'-di-p-toluoyl-L-tartrate, (S)-Netarsudil mono(−)-O,O'-di-p-toluoyl-L-tartrate, (S)-Netarsudil monomesylate, or (S)-Netarsudil dimesylate which is crystalline or amorphous in nature.

Figure 1A:
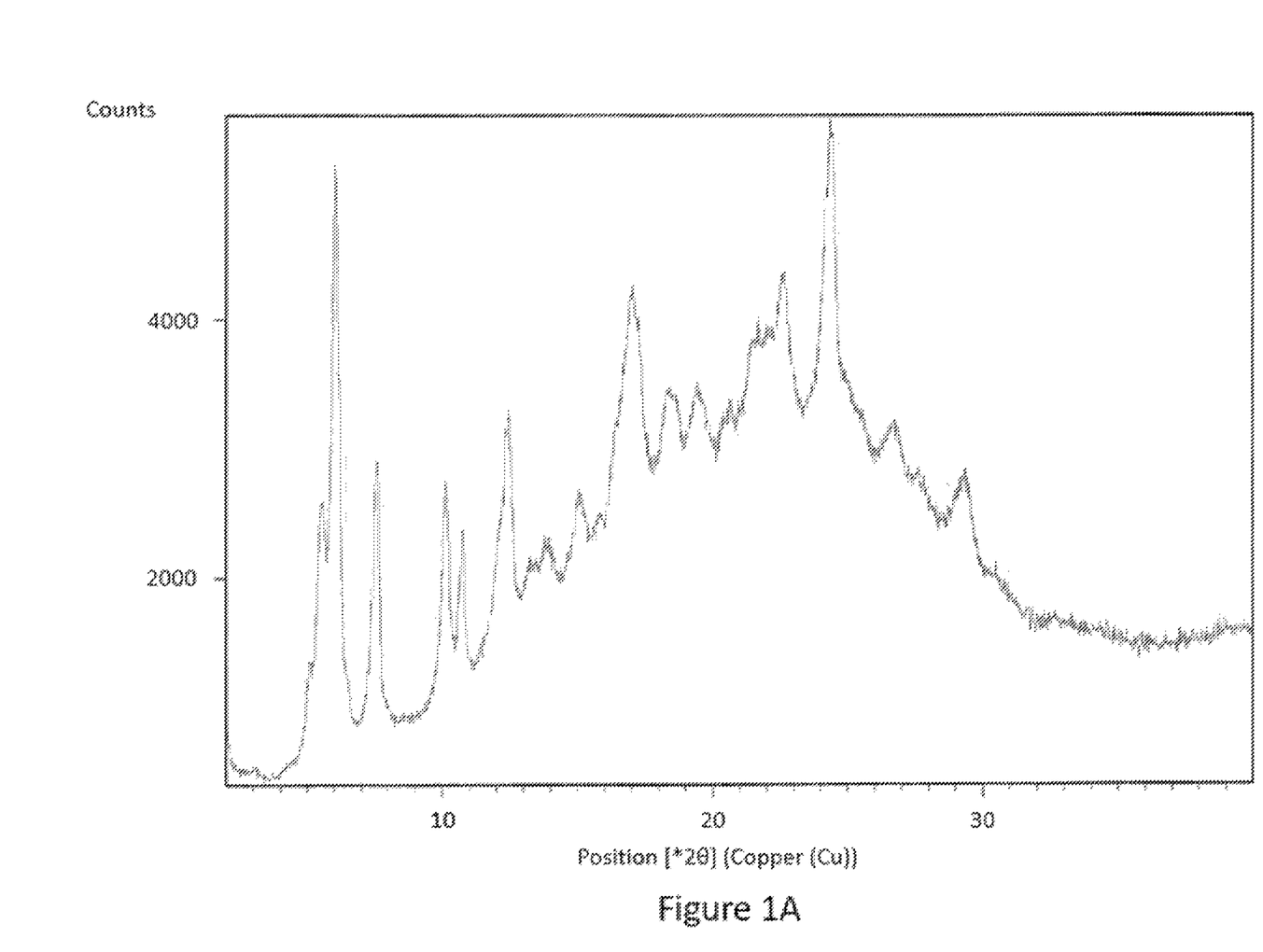
FIG. 1A is the characteristic X-Ray Powder Diffraction (XRPD) pattern of (S)-Netarsudil hemi(−)-O,O′-di-p-toluoyl-L-tartrate salt obtained as per Example 6.
Figure 1B:
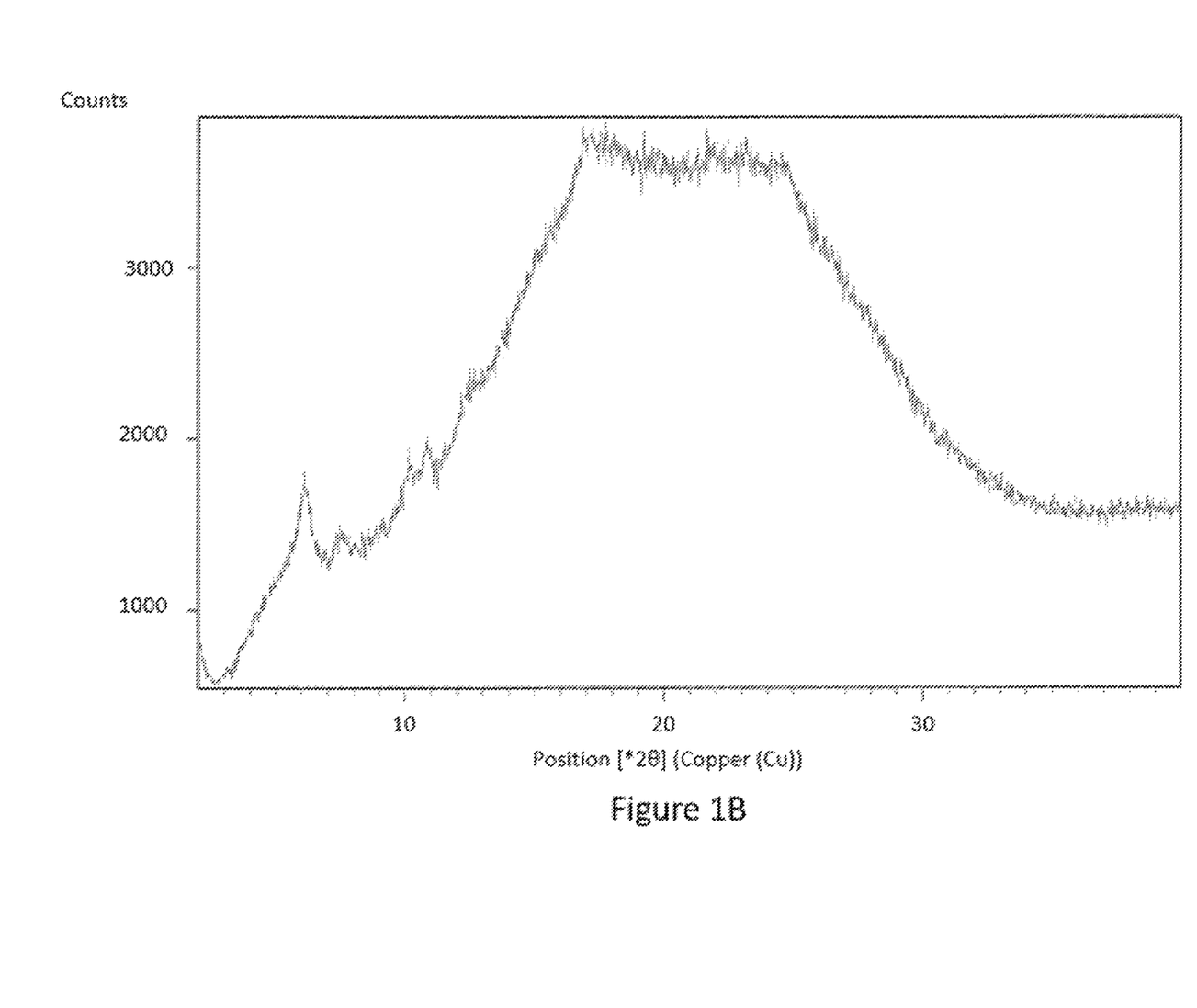
FIG. 1B is the characteristic X-Ray Powder Diffraction (XRPD) pattern of (S)-Netarsudil mono(−)-O, O′-dip-toluoyl-L-tartrate salt obtained as per Example 7.

In one embodiment of this aspect, the crystalline form of (S)-Netarsudil hemi(−)-O,O'-di-p-toluoyl-L-tartrate is characterised by an XRPD pattern having characteristic peaks (2θ values) at 6.07, 17.03, and 24.29 and is further characterised by additional peaks (2θ values) at 5.49, 7.51, 10.13, 12.42 and 22.67±0.2° or as depicted in FIG. 1A. The crystalline form of (S)-Netarsudil mono(−)-O,O'-di-p-toluoyl-L-tartrate is characterised by an XRPD pattern having characteristic peaks (2θ values) at 6.08, 7.41, 10.17, and 10.80±0.2° or as depicted in FIG. 1B.

Figure 2A:
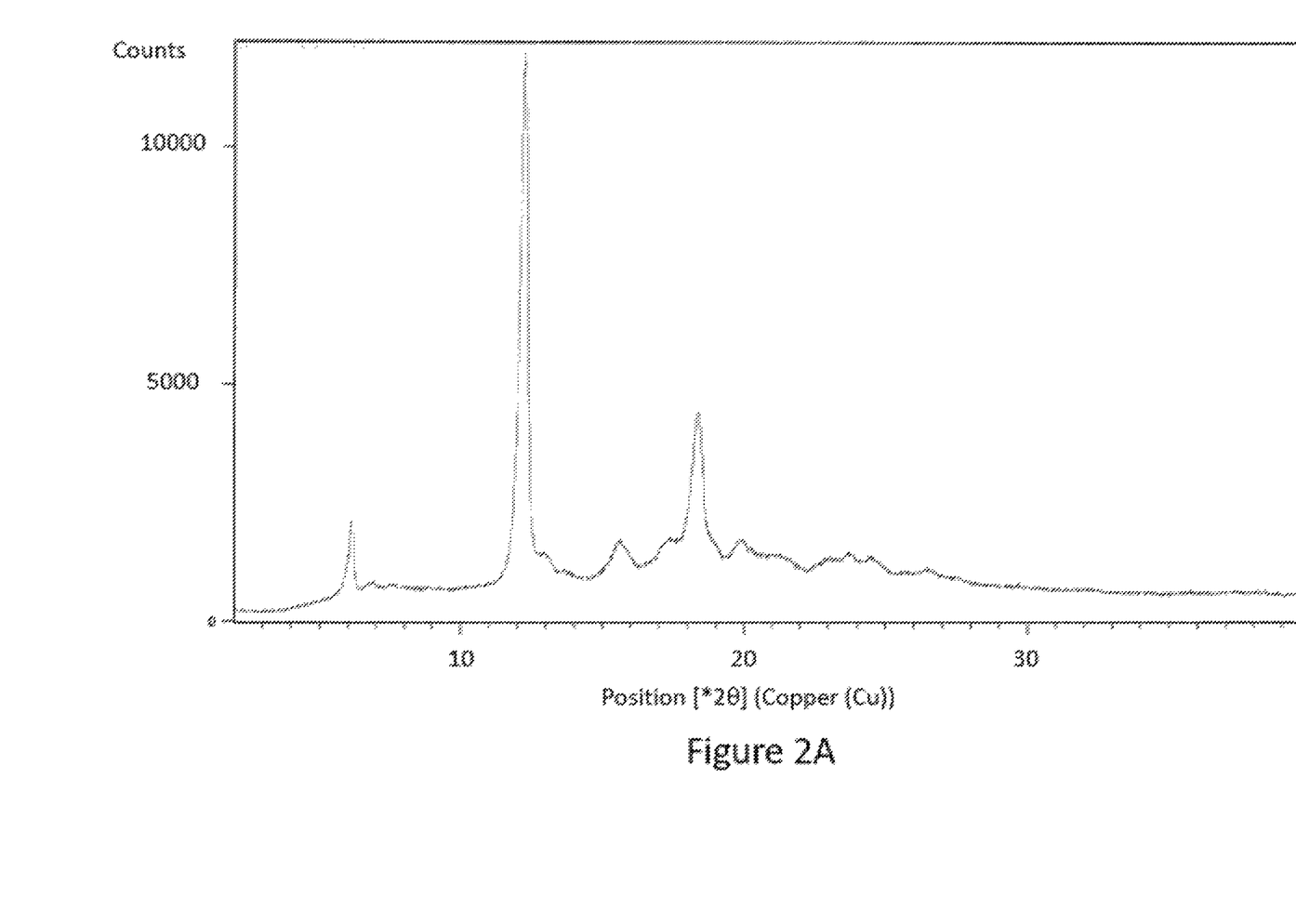
FIG. 2A is the characteristic X-Ray Powder Diffraction (XRPD) pattern of (S)-Netarsudil dimesylate obtained as per Example 9.
Figure 2B:
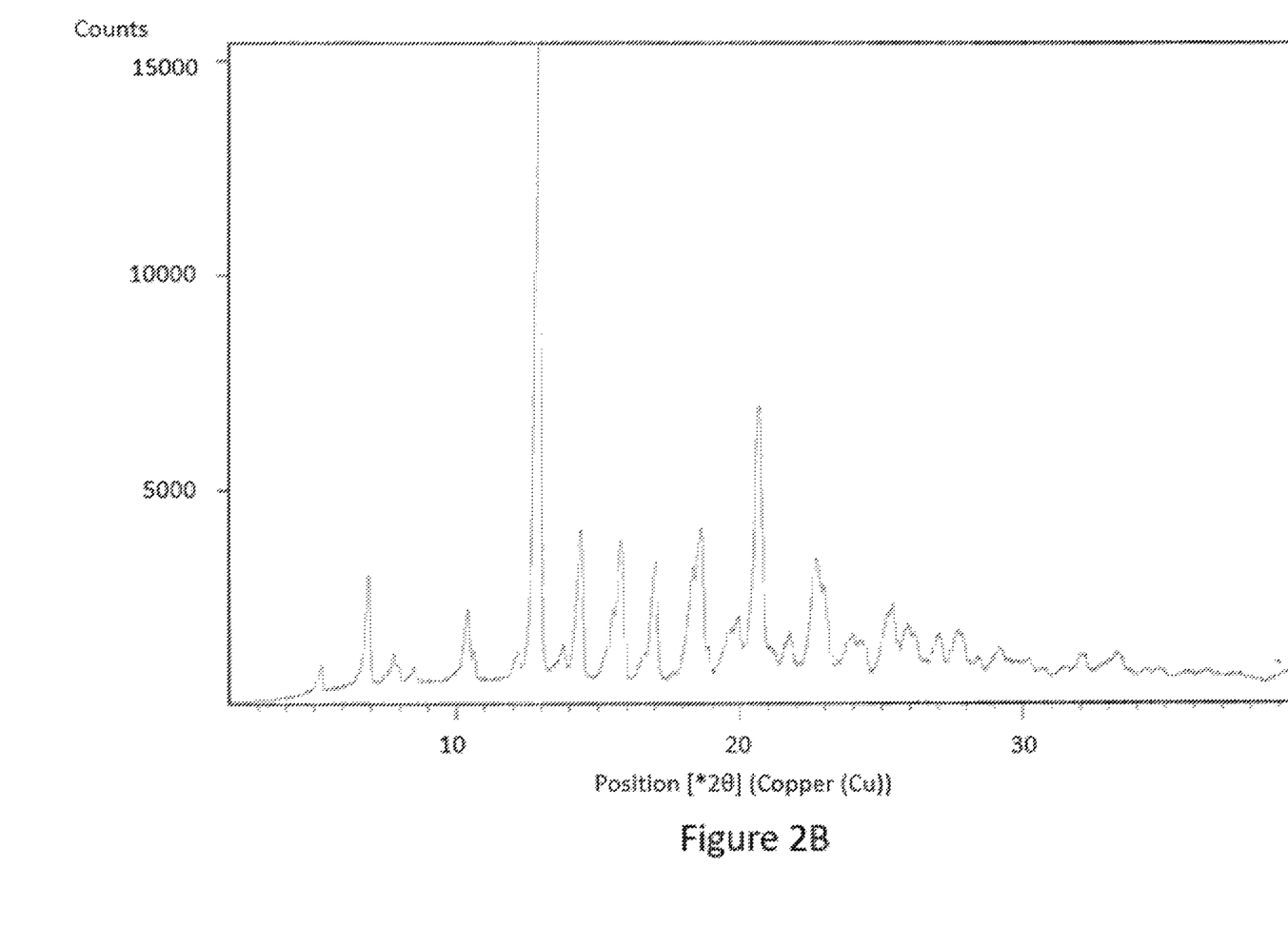
FIG. 2B is the characteristic X-Ray Powder Diffraction (XRPD) pattern of (S)-Netarsudil monomesylate obtained as per Example 10.

In another embodiment of this aspect, the crystalline form of (S)-Netarsudil dimesylate is characterised by an XRPD pattern having characteristic peaks (2θ values) at 6.18, 12.28, and 18.43±0.2 and is further characterised by additional peaks (2θ values) at 13.04, 15.63, 17.38, 19.94, 20.93, and 23.65±0.2° or as depicted in FIG. 2A. The crystalline form of (S)-Netarsudil monomesylate is characterised by an XRPD pattern having characteristic peaks (2θ values) at 12.93, 14.40, and 20.67±0.2° and further characterised by additional peaks (2θ values) at 6.93, 15.82, 17.05, 18.31, 18.64, and 22.70±0.2° or as depicted in FIG. 2B. The crystalline (S)-Netarsudil dimesylate salt of the present invention is highly stable and exhibits improved drying characteristics.

In an embodiment of this aspect, the process for the preparation of said crystalline form of salts of (S)-Netarsudil comprising the steps of, a) obtaining a solution of said salt of (S)-Netarsudil in a solvent selected from $C_1$-$C_4$ alcohol, $C_1$-$C_4$ alkyl ester, or a mixture thereof, b) isolating said crystalline form of salt of (S)-Netarsudil.

In an embodiment, the solution as defined in step (a) is obtained by adding said salt of (S)-Netarsudil as such or by treating (S)-Netarsudil or its salts with methane sulfonic acid or (−)-O,O'-di-p-toluoyl-L-tartaric acid, in a solvent selected from the $C_1$-$C_4$ alcohol, $C_1$-$C_4$ alkyl ester, or a mixture thereof at a temperature of 20° C. to reflux temperature.

In another embodiment, salt of (S)-Netarsudil used in above step (a) can be obtained by the process of the present invention or by using methods known in prior art.

In another embodiment, step (b) involves isolation of said crystalline form of salt of (S)-Netarsudil by common isolation techniques such as cooling, crystallization, precipitation, filtration, filtration under vacuum, decantation and centrifugation, or combinations thereof.

Another aspect of the present invention provides novel intermediates of Formula 2 or its salts which are useful for the preparation of (S)-Netarsudil or its pharmaceutically acceptable salts, Formula 2 wherein $R^1$ is selected from the group consisting of hydrogen, halogen, 2,4-dimethyl benzoyloxy, and hydroxyl; $R^2$ is selected from the group consisting of hydroxyl, $C_1$-$C_5$ alkoxy, halogen, chiral auxiliary group and isoquinolin-6-yl amino.

In an embodiment of this aspect, $R^1$ is hydrogen, and $R^2$ is chiral auxiliary group.

In another embodiment of this aspect, $R^1$ is halogen, and $R^2$ is chiral auxiliary group.

In yet another embodiment of this aspect, $R^1$ is 2,4-dimethyl benzoyloxy, and $R^2$ is chiral auxiliary group.

In still another embodiment of this aspect, $R^1$ is 2,4-dimethyl benzoyloxy, and $R^2$ is isoquinolin-6-yl amino.

Compound of Formula 2 is further converted to (S)-Netarsudil or a pharmaceutically acceptable salts thereof by the methods described herein.

A further aspect of the present invention provides a process for the preparation of Compound of Formula 2 or a salt thereof, Formula 2 wherein $R^1$ is selected from the group consisting of hydrogen, halogen, 2,4-dimethyl benzoyloxy, and hydroxyl; $R^2$ is selected from the group consisting of hydroxyl, $C_1$-$C_5$ alkoxy, halogen, chiral auxiliary group and isoquinolin-6-yl amino;

which comprises reacting a compound of Formula 3 with a compound of Formula 4, Formula 3

-continued

Formula 4 wherein R¹ and Chiral auxiliary group are as defined above, and X is halogen.

Reaction of a compound of Formula 3 with a compound of Formula 4 is performed in the presence of a base as defined above preferably Lithium bis(trimethylsilyl)amide in a suitable solvent at a temperature from −80° C. to reflux temperature.

After the completion of reaction, compound of Formula 2 can be isolated by the common isolation technique such as cooling, extraction, washing, crystallization, precipitation, filtration, filtration under vacuum, decantation and centrifugation, or combinations thereof.

The following examples further elaborate the invention and are not intended to limit the scope of the invention.

EXAMPLES

Example 1: Preparation of 2-[(2S)-2-(4-methylphenyl)-3-oxo-3-[(4R)-2-oxo-4-phenyl-1,3-oxazolidin-3-yl]propyl]-2,3-dihydro-1H-isoindole-1,3-dione (4R)-3-[(4-methylphenyl)acetyl]-4-phenyl-1,3-oxazolidin-2-one (171.5 g) and tetrahydrofuran (750 mL) were mixed and cooled to −65° C. to −70° C. Lithium bis(trimethylsilyl)amide (622 mL) was added to the reaction mixture at −65° C. to −70° C. and was stirred for 2-3 hours. N-bromomethylphthalimide solution (149.2 g in 850 mL of tetrahydrofuran) was charged to the reaction mixture at −65° C. to −70° C. and stirred for 2-3 hours at −30° C. After completion of the reaction, the reaction mixture was quenched with ammonium chloride solution, stirred and filtered the solid. The solid was purified with ethyl acetate & dried to get the titled compound is characterised by mass spectrometry and NMR.

Yield: 126 g
MASS (M+H): 454.9
¹H-NMR (CDCl₃, 400 MHz): δ 7.71-7.58 (m, 4H); 7.23 (d, 2H); 7.15-7.09 (m, 5H); 7.00 (d, 2H); 5.58 (t, 1H); 5.26-5.23 (dd, 1H); 4.43 (t, 1H), 4.10-4.04 (m, 2H), 3.98-3.93 (m, 1H), 2.20 (t, 3H).
¹³C-NMR (CDCl₃, 100 MHz): δ 171.3, 167.7, 152.7, 139.1, 138.0, 134.9, 134.5, 133.9, 131.9, 131.8, 129.5, 129.2, 129.1, 129.0, 128.6, 126.1, 125.8, 124.1, 123.8, 123.7, 123.6, 123.3, 69.7, 57.9, 46.7, 41.1, 21.2.

Example 2: Preparation of 2-[(2S)-2-[4-(bromomethyl) phenyl]-3-oxo-3-[(4R)-2-oxo-4-phenyl-1,3-oxazolidin-3-yl]propyl]-2,3-dihydro-1H-isoindole-1,3-dione Dichloromethane (4 Litre), 2-[(2S)-2-(4-methylphenyl)-3-oxo-3-[(4R)-2-oxo-4-phenyl-1,3-oxazolidin-3-yl]propyl]-2,3-dihydro-1H-isoindole-1,3-dione (100.0 g), 1,3-dibromo-5,5-dimethylhydantoin (31.5 g), azobisisobutyronitrile (18.0 g) were charged in a round bottom flask and was heated to reflux. After completion of reaction, the reaction mixture was quenched with aqueous sodium metabisulfite solution. The layers were separated, extracted with dichloromethane and distilled to get the titled compound is characterised by mass spectrometry and NMR.

Yield: 138 g
MASS (M+2): 535.0
¹H-NMR (CDCl₃, 400 MHz): δ 7.66-7.59 (m, 4H); 7.34 (d, 1H); 7.23 (d, 2H); 7.14-7.10 (m, 5H); 7.01 (d, 1H); 5.65-5.56 (m, 1H); 5.27-5.22 (m, 1H), 4.50-4.39 (m, 1H), 4.36-4.32 (m, 1H), 4.13-4.05 (m, 2H), 3.99-3.94 (m, 1H).

Example 3: Preparation of {4-[(2S)-3-(1,3-dioxo-2,3-dihydro-1H-isoindol-2-yl)-1-oxo-1-[(4R)-2-oxo-4-phenyl-1,3-oxazolidin-3-yl]propan-2-yl]phenyl}methyl-2,4-dimethyl benzoate Acetone (1000 mL), potassium hydroxide (10.57 g), and 2,4-dimethyl benzoic acid (29.7 g) were charged in a round bottom flask and stirred at room temperature. Then potassium iodide (18.2 g), potassium carbonate (30.4 g) and 2-[(2S)-2-[4-(bromomethyl)phenyl]-3-oxo-3-[(4R)-2-oxo-4-phenyl-1,3-oxazolidin-3-yl]propyl]-2,3-dihydro-1H-isoindole-1,3-dione (138 g) were added to the reaction mixture and stirred for 24-28 hours. Water (2 litres) was added to the reaction mixture, stirred and filtered. The crude solid thus obtained was purified in ethyl acetate and dried to obtain the titled compound which is characterised by mass spectrometry and NMR.

Yield: 80.0 g
HPLC purity >99%
MASS (M+NH₄): 620.3
¹H-NMR (DMSO-d₆, 400 MHz): δ 7.84-7.74 (m, 4H); 7.37 (dd, 4H); 7.14-7.05 (m, 7H); 5.77 (t, 1H); 5.45 (dd, 1H); 5.25 (s, 2H); 4.63 (t, 1H), 4.11-4.06 (m, 2H), 3.85-3.80 (m, 1H), 2.46 (s, 3H), 2.32 (s, 3H).
¹³C-NMR (DMSO-d₆, 100 MHz): δ 170.3, 167.2, 166.4, 152.9, 142.5, 139.5, 139.3, 135.9, 135.0, 134.5, 132.3, 131.1, 130.4, 128.6, 128.5, 128.3, 127.8, 126.6, 126.1, 125.3, 123.1, 69.9, 65.4, 57.1, 45.7, 40.8, 21.2, 20.9.

Example 4: Preparation of (2S)-2-{4-[(2,4-dimethylbenzoyloxy)methyl]phenyl}-3-(1,3-dioxo-2,3-dihydro-1H-isoindol-2-yl)propanoic acid Tetrahydrofuran (500 mL) and {4-[(2S)-3-(1,3-dioxo-2,3-dihydro-1H-isoindol-2-yl)-1-oxo-1-[(4R)-2-oxo-4-phenyl-1,3-oxazolidin-3-yl]propan-2-yl]phenyl}methyl-2,4-dimethyl benzoate (50.0 g) were charged in a round bottom flask and cooled to 0-5° C. Hydrogen peroxide (6.0 mole equivalent) was added to the reaction mixture and stirred. Aqueous Lithium hydroxide solution (1.2 mole equivalent) was then added to the reaction mixture at 0-5° C. The reaction mixture was then stirred and the progress of reaction was monitored by TLC. The pH of the reaction mixture was adjusted to less than 2 using aqueous hydrochloric acid. The reaction mixture was extracted by ethyl acetate (2×250 mL) followed by aqueous sodium sulfite solution wash and then with water. The reaction mixture was then distilled out under vacuum and acetic acid was added. The mixture was heated to 80° C. for 4 hours, then added water, stirred, filtered and the solid was dried to obtain the titled compound which is characterised by mass spectrometry and NMR.

Yield: 29 g
HPLC purity >99%
MASS (M+NH₄): 475.1
¹H-NMR (DMSO-d₆, 400 MHz): δ 12.8 (s, 1H); 7.82-7.78 (m, 4H); 7.73 (d, 1H); 7.38-7.29 (dd, 4H); 7.13-7.09 (m, 2H); 5.23 (s, 2H); 4.17-3.99 (m, 3H), 2.44 (s, 3H), 2.31 (s, 3H).

$^{13}$C-NMR (DMSO-d$_6$, 100 MHz): δ 172.6, 167.4, 166.4, 142.4, 139.4, 136.1, 135.5, 134.5, 132.3, 131.2, 130.3, 128.3, 128.2, 126.6, 126.2, 123.1, 65.4, 48.5, 21.2, 20.9.

Example 5: Preparation of {4-[(1S)-2-(1,3-dioxo-2,3-dihydro-1H-isoindol-2-yl)-1-[(isoquinolin-6-yl)carbamoyl]ethyl]phenyl}methyl 2,4-dimethylbenzoate N,N-dimethylformamide (20 mL), and (2S)-2-{4-[(2,4-dimethylbenzoyloxy)methyl]phenyl}-3-(1,3-dioxo-2,3-dihydro-1H-isoindol-2-yl)propanoic acid (25.0 g) were charged in a round bottom flask and was cooled to 0-5° C. 6-aminoisoquinoline (10.25 g), and collidine (10 g) were charged to the reaction mixture followed by 2,2,2-trichloro-1,1-dimethylethyl chloroformate (21.25 g) was added. Reaction mixture was stirred for 1-2 hours. The reaction mixture was quenched with saturated sodium bicarbonate solution and extracted with dichloromethane. Dichloromethane layer was washed with aqueous hydrochloric acid followed by water washing. The reaction mixture was distilled out and treated with ethyl acetate to obtain the titled compound which is characterised by mass spectrometry and NMR.

Yield: 20 g
HPLC purity >98%
MASS (M+H): 584.2
$^1$H-NMR (DMSO-d$_6$, 400 M Hz): δ 11.45 (S, 1H); 9.64 (s, 1H); 8.7 (bs, 1H); 8.53 (d, 1H), 8.39 (d, 1H), 8.29 (d, 1H); 7.96 (dd, 1H); 7.83-7.78 (m, 4H); 7.71 (d, 1H), 7.44 (dd, 4H), 7.11-7.07 (m, 2H), 5.22 (s, 2H); 4.64 (t, 1H), 4.25-4.13 (m, 2H), 2.42 (s, 3H), 2.29 (s, 3H).
$^{13}$C-NMR (DMSO-d$_6$, 100 MHz): δ 170.9, 167.5, 166.3, 146.1, 144.8, 142.4, 139.5, 139.4, 136.4, 135.7, 134.5, 133.0, 132.3, 131.3, 131.2, 130.3, 128.3, 128.2, 126.6, 126.1, 123.6, 123.5, 123.1, 113.0, 65.4, 49.7, 21.2, 20.9.

Example 6: Preparation of (S)-Netarsudil hemi(−)-O,O'-di-p-toluoyl-L-tartrate Salt Ethanol (80 mL) and {4-[(1S)-2-(1,3-dioxo-2,3-dihydro-1H-isoindol-2-yl)-1-[(isoquinolin-6-yl)carbamoyl]ethyl]phenyl}methyl 2,4-dimethylbenzoate (5 g) were charged in the flask and cooled to 0° C. Hydrazine hydrate (13.7 mL) was added to the reaction mixture and stirred for 2-3 hours. Ethanol was distilled out under vacuum below 45° C., then dichloromethane (50 mL) and water (100 mL) was charged, stirred and separated layers. Dichloromethane was distilled out completely and the residue was dissolved in isopropyl alcohol (30 mL). (−)-di-p-toluoyl-L-tartaric acid (2.95 g dissolved in 10 mL of methanol) was then added to the mixture. The reaction mixture was stirred for 2 hours, filtered the solid, and dried under vacuum at 50° C. to obtain the titled compound.

Yield: 4.0 g
HPLC purity >99%
Chiral purity >99% ee
(S)-Netarsudil hemi(−)-O,O'-di-p-toluoyl-L-tartrate salt obtained above is characterised by PXRD as depicted in FIG. 1A.

Example 7: Preparation of (S)-Netarsudil mono(−)-O,O'-di-p-toluoyl-L-tartrate salt (S)-Netarsudil hemi(−)-O, O'-dip-toluoyl-L-tartrate salt (5 g) was charged to dichloromethane (50 mL) at 20-30° C. in round bottom flask. Concentrated ammonia solution (25 mL) was charged to the flask at 20-30° C. and stirred for 30 minutes. The layers were separated and the dichloromethane layer was washed with water (50 mL). Dichloromethane was distilled under vacuum at 40-45° C. and degassed for 30 minutes. Methanol (40 mL) was charged into the flask at 20-30° C. and (−)-di-p-toluoyl-L-tartaric acid (2.98 g dissolved in Methanol 20 mL) was added to it at 20-30° C. The mixture was heated to 60-65° C. and stirred for 2 hours at 60-65° C. The reaction mixture was distilled completely under vacuum at 50-60° C. and then isopropanol (20 ml) was charged at 50-60° C. The mixture was again distilled completely under vacuum at 50-60° C. and then degassed for 1 hour at 50-60° C. under vacuum to obtain the titled compound.

(S)-Netarsudil mono(−)-O,O'-di-p-toluoyl-L-tartrate salt obtained above is characterised by PXRD as depicted in FIG. 1B.

Example 8: Preparation of (S)-Netarsudil Dimesylate (S)-Netarsudil (−)-O,O'-di-p-toluoyl-L-tartrate salt (1.0 g), and dichloromethane (50 mL) were charged in the flask at 20-30° C. Aqueous ammonia was added & stirred for 30 minutes. The layers were separated and dichloromethane layer was distilled under vacuum at 40-45° C. Isopropanol (20 mL) was charged in the flask at 20-30° C. Methane sulfonic acid (0.27 g dissolved in Isopropanol 10 mL) was then added at 0-10° C. and stirred at 0-10° C. The reaction mixture was filtered, washed with chilled Isopropanol (10 mL) and dried the solid under vacuum at 60° C. for 24 hours to obtain the titled compound.

Yield: 0.7 g
HPLC purity >99%
Chiral purity >99% ee

Example 9: Preparation of Crystalline Form of (S)-Netarsudil Dimesylate

Ethyl acetate (7.2 mL) was charged in round bottom flask and then (S)-Netarsudil dimesylate obtained in Example 8 was added at 20-30° C. The mixture was stirred for 1-2 hours at 20-30° C. and filtered under nitrogen and washed with ethyl acetate. The solid was dried under vacuum at 70-80° C. for 15-20 hours to obtain the title compound.

Figure 3:
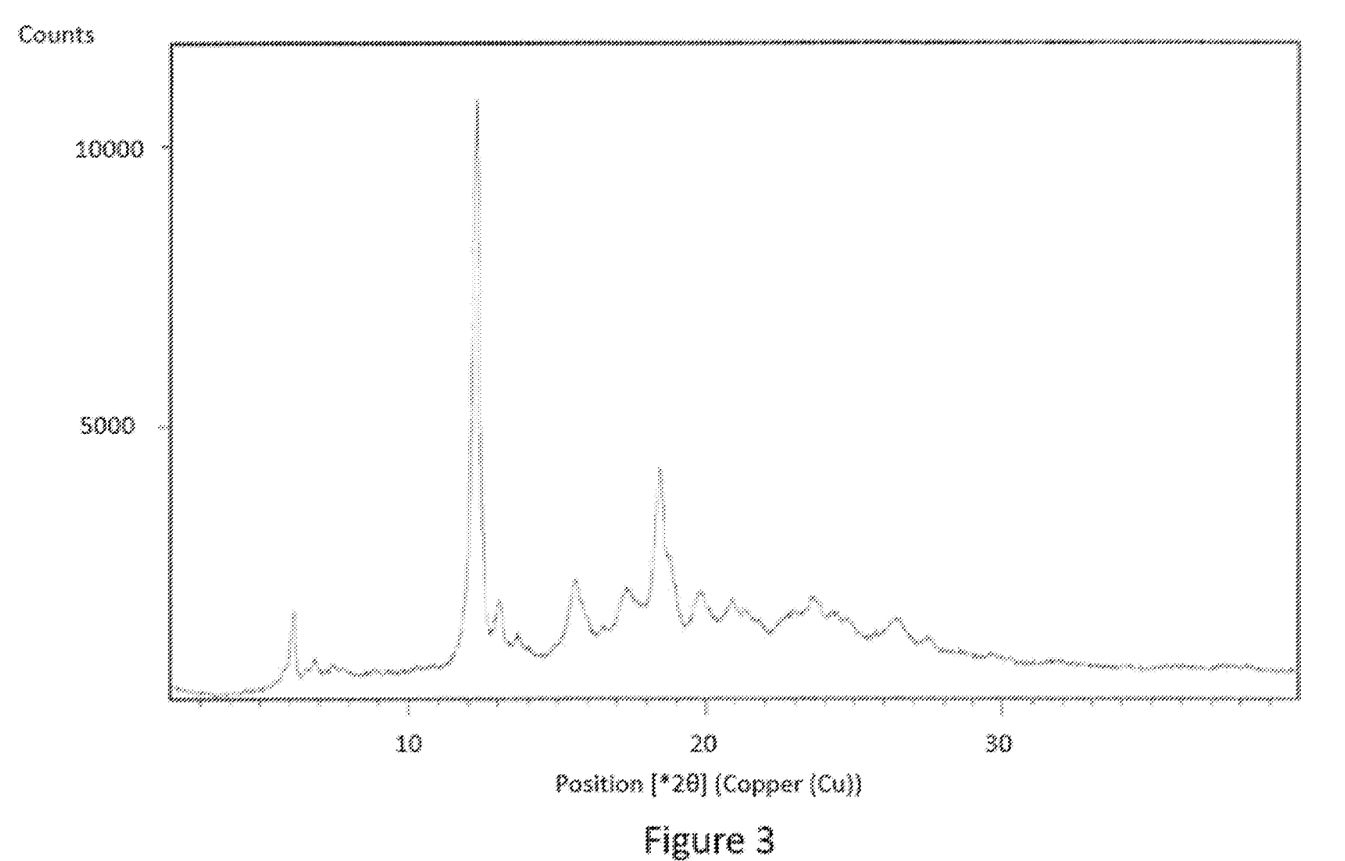
FIG. 3 is the characteristic X-Ray Powder Diffraction (XRPD) pattern of (S)-Netarsudil dimesylate stored at room temperature (RT) for 6 months.

(S)-Netarsudil dimesylate obtained above is characterised by PXRD as depicted in FIG. 2A. The said crystalline form of (S)-Netarsudil dimesylate is stable for at least 6 months when stored at RT. The XRD of Crystalline form of (S)-Netarsudil dimesylate which is stored for 6 months at RT is provided in FIG. 3.

Example 10: Preparation of (S)-Netarsudil Monomesylate (S)-Netarsudil hemi(−)-O,O'-di-p-toluoyl-L-tartrate salt (5.0 g) was charged to dichloromethane (50 mL) in the flask at 20-30° C. Concentrated ammonia solution (25 mL) was charged in the flask at 20-30° C. and stirred for 30 minutes. The layers were separated and the dichloromethane layer was washed with water (50 mL). Dichloromethane was distilled under vacuum at 40-45° C. and degassed for 30 minutes. Methanol (30 mL) was charged in the flask at 20-30° C. and the mixture was cooled to 0-10° C. Methane sulfonic acid (0.74 g dissolved in ethyl acetate 20 mL) was charged in the flask at 0-10° C. and stirred for 2 hours at 0-10° C. The reaction mixture was distilled out completely under vacuum at 50-60° C. and dried under vacuum at 60-70° C. for 12 hours to obtain the titled compound. (S)-Netarsudil monomesylate salt obtained above is characterised by PXRD as depicted in FIG. 2B.

While considerable emphasis has been placed herein on the specific elements of the preferred embodiment, it will be appreciated that many alterations can be made and that many modifications can be made in preferred embodiment without departing from the principles of the invention. These and other changes in the preferred embodiments of the invention will be apparent to those skilled in the art from the disclosure herein, whereby it is to be distinctly understood that the foregoing descriptive matter is to be interpreted merely as illustrative of the invention and not as a limitation.

That which is claimed:

1. A process for the preparation of (S)-Netarsudil of Formula 1 or its pharmaceutically acceptable salts thereof, Formula 1 comprising conversion of compound of Formula 2 or a salt thereof to (S)-Netarsudil or its pharmaceutically acceptable salts, Formula 2 wherein $R^1$ is selected from the group consisting of hydrogen, halogen, 2,4-dimethyl benzoyloxy, and hydroxyl; and $R^2$ is selected from the group consisting of hydroxyl, $C_1$-$C_5$ alkoxy, halogen, a chiral auxiliary group and isoquinolin-6-yl-amino.

2. The process according to claim 1 comprising first obtaining a compound of Formula 2 wherein $R^1$ is 2,4-dimethyl benzoyloxy and $R^2$ is isoquinolin-6-yl amino followed by deprotection.

3. The process according to claim 2 comprising converting a compound of Formula 2 having $R^1$ as hydrogen to $R^1$ as 2,4-dimethyl benzoyloxy through halogenation followed by esterification with 2,4-dimethyl benzoic acid.

4. The process according to claim 3, wherein the halogenation is performed with a halogenating agent in a solvent at a temperature from about 20° C. to reflux temperature.

5. The process according to claim 3, wherein the halogenation is performed in the presence of a radical initiator selected from the group of inorganic peroxide, organic peroxide, and azo compounds.

6. The process according to claim 3, wherein the esterification is performed in the presence of a base in a solvent at a temperature from about 20° C. to reflux temperature.

7. The process according to claim 2, wherein the compound of Formula 2 having $R^2$ as a chiral auxiliary is converted to $R^2$ as isoquinolin-6-yl amino through hydrolysis followed by condensation with 6-aminoisoquinoline.

8. The process according to claim 7, wherein the hydrolysis is performed with an alkali metal hydroperoxide.

9. The process according to claim 7, wherein the condensation is performed in the presence of a coupling agent.

10. The process according to claim 2, wherein the deprotection is performed with a deprotecting agent in a solvent at a temperature from about –20° C. to reflux temperature.

11. A compound of Formula 2 or its salt,

Formula 2 wherein R' is selected from the group consisting of hydrogen, halogen, 2,4-dimethyl benzoyloxy, and hydroxyl; and $R^2$ is selected from the group consisting of hydroxyl, $C_1$-$C_5$ alkoxy, halogen, a chiral auxiliary group, and isoquinolin-6-yl amino.

12. A process for the preparation of compound of Formula 2 according to claim 11, comprising reacting a compound of Formula 3 with a compound of Formula 4, Formula 3

Formula 4 wherein $R^1$ is selected from the group consisting of hydrogen, halogen, 2,4-dimethyl benzoyloxy, and hydroxyl; X is halogen; and the chiral auxiliary group is a non-racemic functional group.

13. The process according to claim 12, wherein the process is performed in the presence of a base in a solvent at a temperature from about –80° C. to reflux temperature.

14. A salt of (S)-Netarsudil, wherein the salt is a (S)-Netarsudil hemi(–)-O,O'-di-p-toluoyl-L-tartrate, (S)-Netarsudil mono(–)-O,O'-di-p-toluoyl-L-tartrate, or (S)-Netarsudil monomesylate.

15. The salt according to claim 14, wherein the said (S)-Netarsudil monomesylate salt is a crystalline form characterised by an XRPD pattern having characteristic peaks (2θ values) at 12.93, 14.40, and 20.67±0.2° or as depicted in FIG. 2B.

16. A crystalline form of (S)-Netarsudil dimesylate characterised by an XRPD pattern having characteristic peaks (2θ values) at 6.18, 12.28, and 18.43±0.2° or as depicted in FIG. 2A.

17. The crystalline form of (S)-Netarsudil dimesylate according to claim 16, wherein the XRPD pattern is further characterised by peaks (2θ values) at 13.04, 15.63, 17.38, 19.94, 20.93, and 23.65±0.2°.

18. The process for the preparation of crystalline form of (S)-Netarsudil monomesylate according to claim 15 or crystalline form of (S)-Netarsudil dimesylate characterised by an XRPD pattern as depicted in FIG. 2A, comprising the steps of, a) obtaining a solution of said salt of (S)-Netarsudil in a solvent selected from $C_1$-$C_4$ alcohol, $C_1$-$C_4$ alkyl ester, or a mixture thereof, b) isolating crystalline form of said salts of (S)-Netarsudil.

19. The process according to claim 18, wherein the solution of step (a) is obtained by treating (S)-Netarsudil or salt thereof with methane sulfonic acid in a solvent selected from $C_1$-$C_4$ alcohol, $C_1$-$C_4$ alkyl ester, or a mixture thereof.

20. The process according to claim 18, wherein the isolation in step (b) involves cooling, crystallization, precipitation, filtration, filtration under vacuum, decantation and centrifugation, or combinations thereof.

* * * * *